(12) United States Patent
Coulomb et al.

(10) Patent No.: US 11,396,489 B2
(45) Date of Patent: Jul. 26, 2022

(54) CYCLOHEXENE PROPANAL DERIVATIVES AS PERFUMING INGREDIENTS

(71) Applicant: Firmenich SA, Satigny (CH)

(72) Inventors: Julien Coulomb, Satigny (CH); Anthony Alexander Birkbeck, Satigny (CH); Julie Quintaine, Satigny (CH)

(73) Assignee: Firmenich SA, Satigny (CH)

( * ) Notice: Subject to any disclaimer, the term of this patent is extended or adjusted under 35 U.S.C. 154(b) by 0 days.

(21) Appl. No.: 16/975,038

(22) PCT Filed: Jun. 24, 2019

(86) PCT No.: PCT/EP2019/066638
§ 371 (c)(1),
(2) Date: Aug. 21, 2020

(87) PCT Pub. No.: WO2020/002212
PCT Pub. Date: Jan. 2, 2020

(65) Prior Publication Data
US 2021/0101860 A1    Apr. 8, 2021

(30) Foreign Application Priority Data

Jun. 26, 2018  (EP) .................... 18179844

(51) Int. Cl.
C07C 47/267 (2006.01)
C11B 9/00 (2006.01)

(52) U.S. Cl.
CPC .......... C07C 47/267 (2013.01); C11B 9/0034 (2013.01)

(58) Field of Classification Search
CPC ...... C07C 47/267; C07C 47/27; C11B 9/0034
See application file for complete search history.

(56) References Cited

FOREIGN PATENT DOCUMENTS

| EP | 2578671 A1 | 4/2013 |
| GB | 1568998 A | 6/1980 |
| WO | WO-2017009175 A1 * | 1/2017 .......... C11B 9/0061 |

OTHER PUBLICATIONS

International Search Report for International Patent Application No. PCT/EP2019/066638, dated Sep. 27, 2019, 2 pages.
Bône et al. "Microencapsulated Fragrances in Melamine Formaldehyde Resins," CHIMIA 2011, 65, No. 3, 177-181.
Dietrich et al. "Amino resin microcapsules: I. Literature and patent review", Acta Polymerica 40 (1989) No. 4, 243-251.
Dietrich et al. "Amino resin microcapsules: II: Preparation and morphology", Acta Polymerica 40 (1989) No. 5, 325-331.
Bonatz et al. "Amino resin microcapsules: III. Release Properties", Acta Polymerica 40 (1989) No. 11, 683-690.
Dietrich et al. "Amino resin microcapsules: IV: Surface tension of the resins and mechanism of capsule formation", Acta Polymerica 41 (1990) No. 2, 91-95.
Lee et al. "Microencapsulation of fragrant oil via in situ polymerization: effects of pH and melamine-formaldehyde molar ratio" Journal of Microencapsulation, 2002, 19:5, 559-569.

* cited by examiner

*Primary Examiner* — Arrie L Reuther
(74) *Attorney, Agent, or Firm* — Armstrong Teasdale LLP

(57) ABSTRACT

Described herein is a compound of formula (I)

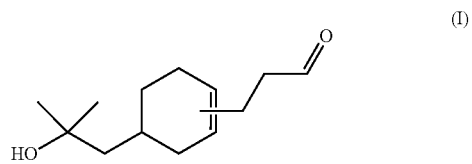

in the form of any one of its stereoisomers, regioisomers or a mixture thereof. The use of compound of formula (I) as perfuming ingredients of floral type and of these compounds as part of a perfuming composition or of a perfuming consumer product are also described.

11 Claims, No Drawings

CYCLOHEXENE PROPANAL DERIVATIVES AS PERFUMING INGREDIENTS

CROSS-REFERENCE TO RELATED APPLICATIONS

This application is a U.S. National Phase Application of International Patent Application No. PCT/EP2019/066638, filed Jun. 24, 2019, which claims the benefit of priority to European Patent Application No. 18179844.8, filed Jun. 26, 2018, the entire contents of each of which are hereby incorporated by reference herein.

TECHNICAL FIELD

The present invention relates to the field of perfumery. More particularly, the present invention relates to the use as perfuming ingredient of compounds of formula (I) as defined below, which are particularly useful perfuming ingredients of the floral type. Moreover, the present invention relates to a perfuming composition or a perfumed consumer product comprising the compounds of formula (I).

BACKGROUND

One of the key ingredients in the perfumery industry are the one imparting a floral impression and in particular a lily of the valley odor. Said note is very appreciated and used in a multitude of perfumed consumer products. Lilial® (2-methyl-3-[4-(2-methyl-2-propanyl)phenyl]propanal, trademark from Givaudan-Roure SA, Vernier, Suisse) and Lyral® (4/3-(4-hydroxy-4-methylpentyl)-3-cyclohexene-1-carbaldehyde; origin International Flavors & Fragrances, USA) are both common ingredients used for this purpose. Lilial® possesses a lily of the valley odor with watery connotations while Lyral® imparts floral, lily of the valley, hydroxycitronellal odor notes quite different from the notes of Lilial®. However, both ingredients have been limited due to various reasons.

So, there is a constant need to develop novel perfuming ingredients imparting floral and in particular lily of valley notes.

One related structural analogue of compound of formula (I) has been reported in WO 2017009175 as a perfuming ingredient characterized by having a nice and well balanced floral, lily of the valley, hydroxycitronellal odor note, and an overall olfactive character strongly reminiscent of the one of the very well-known ingredients, Lyral®. Said analogue being 3-[4-(2-hydroxy-2-methylpropyl)phenyl]propanal possesses an aromatic phenyl moiety i.e. a different chemical structure from the present invention's compound.

The prior art document does not report the compound of formula (I) nor suggest any organoleptic properties of such compound of formula (I), or any use of said compounds in the field of perfumery.

SUMMARY OF THE INVENTION

The invention relates to compound of formula (I) which imparts an odor of the floral type, in particular lily of the valley (also named muguet) which is much appreciated in perfumery.

A first object of the present invention is a compound of formula

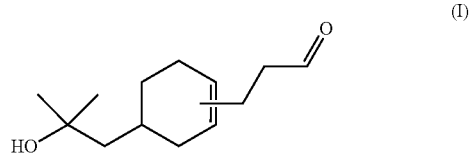

in the form of any one of its stereoisomers, regioisomers or a mixture thereof.

A second object of the present invention is a method to confer, enhance, improve or modify the odor properties of a perfuming composition or of a perfumed article, which method comprises adding to said composition or article an effective amount of at least a compound of formula (I) as defined above.

A third object of the present invention is the use as a perfuming ingredient of a compound of formula (I) as defined above.

Another object of the present invention is a perfuming composition comprising
i) at least one compound of formula (I), as defined above;
ii) at least one ingredient selected from the group consisting of a perfumery carrier and a perfumery base; and
iii) optionally at least one perfumery adjuvant.

A last object of the present invention is a perfumed consumer product comprising at least one compound of formula (I) or a composition as defined above.

DESCRIPTION OF THE INVENTION

Surprisingly, it has now been discovered that a compound of formula (I) presents a floral, Lily of the valley and lilac odor, and imparts to a perfuming composition a floral-green, rose and ozonic note which is particularly appreciated.

A first object of the present invention is a compound of formula

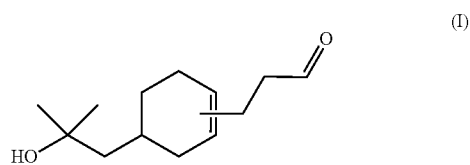

in the form of any one of its stereoisomers, regioisomers or a mixture thereof. Said compounds can be used as perfuming ingredients presenting a floral, Lily of the valley and lilac odor. Said compounds can also be used as perfuming ingredients for instance to impart floral-green, rosy and ozonic notes.

For the sake of clarity, by the expression "any one of its stereoisomers, regioisomers or a mixture thereof" it is meant that the invention's compounds can be in "any one of its stereoisomers or a mixture thereof" and/or "any one of its regioisomers or a mixture thereof".

For the sake of clarity, by the expression "any one of its stereoisomers or a mixture thereof", or the similar, it is meant the normal meaning understood by a person skilled in the art, i.e. that the invention's compound can be a pure enantiomer, a mixture of enantiomers or a racemate.

For the sake of clarity, by the expression "any one of its regioisomers or a mixture thereof", it is meant the normal meaning understood by a person skilled in the art, i.e. that the propanal moiety attached to the olefinic double bond can be substituted on any one of the carbons of the indicated olefinic double bond of the compound of formula (I).

According to any one of the above embodiments, the compound of the present invention is of formula

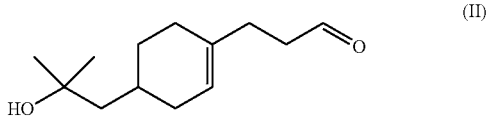

(II)

in the form of any one of its stereoisomers or a mixture thereof.

In other words, according to any one of the above embodiments of the invention, the compound of formula (I) may be selected from 3-(4-(2-hydroxy-2-methylpropyl)cyclohex-1-en-1-yl)propanal.

As specific examples of the invention's compound, one may cite, as non-limiting example, 3-(4-(2-hydroxy-2-methylpropyl)cyclohex-1-en-1-yl)propanal which has a more floral-green, rose, ozonic organoleptic impression.

When the odor of the invention's compound is compared with that of the prior art compound 3-[4-(2-hydroxy-2-methylpropyl)phenyl]propanal, then the invention's compound also possesses a floral, Lily of the valley and lilac odor, but imparts to a perfuming composition a more floral-green, rosy, ozonic organoleptic impression. The invention's compound contrary to the prior art compound harmonizes very well with green and rosy notes.

According to any one of the above embodiments of the invention, the compound of formula (I) can be a mixture of the regioisomers of compounds of formula (I), in particular a mixture of

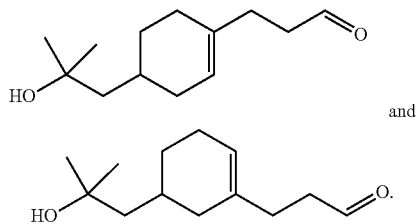

and

According to a particular embodiment of the invention, the mixture of the regioisomers is used in a weight ratio of

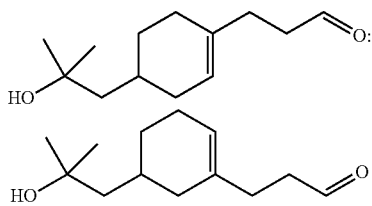

of 90-50:10-50, more preferably 80-60:20-40 and even more preferably of 75-65:25-35.

As mentioned above, the invention concerns the use as perfuming ingredient of a compound of formula (I). In other words, it concerns a method or a process to confer, enhance, improve or modify the odor properties of a perfuming composition or of a perfumed article or of a surface, which method comprises adding to said composition or article an effective amount of at least a compound of formula (I), e.g. to impart its typical note. Understood that the final hedonic effect may depend on the precise dosage and on the organoleptic properties of the invention's compound, but the addition of the invention's compound will impart to the final product its typical touch in the form of a note, touch or aspect depending on the dosage.

By "use of a compound of formula (I)" it has to be understood here also the use of any composition containing a compound of formula (I) and which can be advantageously employed in the perfumery industry.

Said compositions, which in fact can be advantageously employed as perfuming ingredients, are also an object of the present invention.

Therefore, another object of the present invention is a perfuming composition comprising:
i) as a perfuming ingredient, at least one invention's compound as defined above;
ii) at least one ingredient selected from the group consisting of a perfumery carrier and a perfumery base; and
iii) optionally at least one perfumery adjuvant.

By "perfumery carrier" it is meant here a material which is practically neutral from a perfumery point of view, i.e. that does not significantly alter the organoleptic properties of perfuming ingredients. Said carrier may be a liquid or a solid.

As liquid carrier one may cite, as non-limiting examples, an emulsifying system, i.e. a solvent and a surfactant system, or a solvent commonly used in perfumery. A detailed description of the nature and type of solvents commonly used in perfumery cannot be exhaustive. However, one can cite as non-limiting examples, solvents such as butylene or propylene glycol, glycerol, dipropyleneglycol and its monoether, 1,2,3-propanetriyl triacetate, dimethyl glutarate, dimethyl adipate 1,3-diacetyloxypropan-2-yl acetate, diethyl phthalate, isopropyl myristate, benzyl benzoate, benzyl alcohol, 2-(2-ethoxyethoxy)-1-ethano, tri-ethyl citrate or mixtures thereof, which are the most commonly used. For the compositions which comprise both a perfumery carrier and a perfumery base, other suitable perfumery carriers than those previously specified, can be also ethanol, water/ethanol mixtures, limonene or other terpenes, isoparaffins such as those known under the trademark Isopar® (origin: Exxon Chemical) or glycol ethers and glycol ether esters such as those known under the trademark Dowanol® (origin: Dow Chemical Company), or hydrogenated castors oils such as those known under the trademark Cremophor® RH 40 (origin: BASF).

Solid carrier is meant to designate a material to which the perfuming composition or some element of the perfuming composition can be chemically or physically bound. In general such solid carriers are employed either to stabilize the composition, or to control the rate of evaporation of the compositions or of some ingredients. The use of solid carrier is of current use in the art and a person skilled in the art knows how to reach the desired effect. However by way of non-limiting example of solid carriers, one may cite absorbing gums or polymers or inorganic material, such as porous polymers, cyclodextrins, wood based materials, organic or inorganic gels, clays, gypsum talc or zeolites.

As other non-limiting examples of solid carriers, one may cite encapsulating materials. Examples of such materials may comprise wall-forming and plasticizing materials, such as mono, di- or trisaccharides, natural or modified starches, hydrocolloids, cellulose derivatives, polyvinyl acetates, polyvinylalcohols, proteins or pectins, or yet the materials cited in reference texts such as H. Scherz, Hydrokolloide: Stabilisatoren, Dickungs- and Geliermittel in Lebensmitteln, Band 2 der Schriftenreihe Lebensmittelchemie, Lebensmittelqualität, Behr's Verlag GmbH & Co., Hamburg, 1996. The encapsulation is a well-known process to a person skilled in the art, and may be performed, for instance, by using techniques such as spray-drying, agglomeration or yet extrusion; or consists of a coating encapsulation, including coacervation and complex coacervation technique.

As non-limiting examples of solid carriers, one may cite in particular the core-shell capsules with resins of aminoplast, polyamide, polyester, polyurea or polyurethane type or a mixture thereof (all of said resins are well known to a person skilled in the art) using techniques like phase separation process induced by polymerization, interfacial polymerization, coacervation or altogether (all of said techniques have been described in the prior art), optionally in the presence of a polymeric stabilizer or of a cationic copolymer.

Resins may be produced by the polycondensation of an aldehyde (e.g. formaldehyde, 2,2-dimethoxyethanal, glyoxal, glyoxylic acid or glycolaldehyde and mixtures thereof) with an amine such as urea, benzoguanamine, glycoluryl, melamine, methylol melamine, methylated methylol melamine, guanazole and the like, as well as mixtures thereof. Alternatively one may use preformed resins alkylolated polyamines such as those commercially available under the trademark Urac® (origin: Cytec Technology Corp.), Cymel® (origin: Cytec Technology Corp.), Urecoll® or Luracoll® (origin: BASF).

Others resins one are the ones produced by the polycondensation of a polyol, like glycerol, and a polyisocyanate, like a trimer of hexamethylene diisocyanate, a trimer of isophorone diisocyanate or xylylene diisocyanate or a Biuret of hexamethylene diisocyanate or a trimer of xylylene diisocyanate with trimethylolpropane (known with the tradename of Takenate®, origin: Mitsui Chemicals), among which a trimer of xylylene diisocyanate with trimethylolpropane and a Biuret of hexamethylene diisocyanate.

Some of the seminal literature related to the encapsulation of perfumes by polycondensation of amino resins, namely melamine based resins with aldehydes includes represented by articles such as those published by K. Dietrich et al. *Acta Polymerica,* 1989, vol. 40, pages 243, 325 and 683, as well as 1990, vol. 41, page 91. Such articles already describe the various parameters affecting the preparation of such core-shell microcapsules following prior art methods that are also further detailed and exemplified in the patent literature. U.S. Pat. No. 4,396,670, to the Wiggins Teape Group Limited is a pertinent early example of the latter. Since then, many other authors have enriched the literature in this field and it would be difficult to cover all published developments here, but the general knowledge in encapsulation technology is very significant. More recent publications of pertinency, which disclose suitable uses of such microcapsules, are represented for example by the article of H. Y. Lee et al. *Journal of Microencapsulation,* 2002, vol. 19, pages 559-569, international patent publication WO 01/41915 or yet the article of S. Bône et al. *Chimia,* 2011, vol. 65, pages 177-181.

By "perfumery base" what is meant here is a composition comprising at least one perfuming co-ingredient.

Said perfuming co-ingredient is not of formula (I). Moreover, by "perfuming co-ingredient" it is meant here a compound, which is used in a perfuming preparation or a composition to impart a hedonic effect. In other words such a co-ingredient, to be considered as being a perfuming one, must be recognized by a person skilled in the art as being able to impart or modify in a positive or pleasant way the odor of a composition, and not just as having an odor.

The nature and type of the perfuming co-ingredients present in the base do not warrant a more detailed description here, which in any case would not be exhaustive, the skilled person being able to select them on the basis of his general knowledge and according to the intended use or application and the desired organoleptic effect. In general terms, these perfuming co-ingredients belong to chemical classes as varied as alcohols, lactones, aldehydes, ketones, esters, ethers, acetates, nitriles, terpenoids, nitrogenous or sulphurous heterocyclic compounds and essential oils, and said perfuming co-ingredients can be of natural or synthetic origin.

In particular one may cite perfuming co-ingredients which are commonly used in perfume formulations, such as:

Aldehydic ingredients: decanal, dodecanal, 2-methyl-undecanal, 10-undecenal, octanal and/or nonenal;

Aromatic-herbal ingredients: eucalyptus oil, camphor, eucalyptol, menthol and/or alpha-pinene;

Balsamic ingredients: coumarine, ethylvanillin and/or vanillin;

Citrus ingredients: dihydromyrcenol, citral, orange oil, linalyl acetate, citronellyl nitrile, orange terpenes, limonene, 1-P-menthen-8-yl acetate and/or 1,4(8)-P-menthadiene;

Floral ingredients: Methyl dihydrojasmonate, linalool, citronellol, phenylethanol, 3-(4-tert-butylphenyl)-2-methylpropanal, hexylcinnamic aldehyde, benzyl acetate, benzyl salicylate, tetrahydro-2-isobutyl-4-methyl-4(2H)-pyranol, beta ionone, methyl 2-(methylamino)benzoate, (E)-3-methyl-4-(2,6,6-trimethyl-2-cyclohexen-1-yl)-3-buten-2-one, hexyl salicylate, 3,7-dimethyl-1,6-nonadien-3-ol, 3-(4-isopropylphenyl)-2-methylpropanal, verdyl acetate, geraniol, P-menth-1-en-8-ol, 4-(1,1-dimethylethyl)-1-cyclohexyle acetate, 1,1-dimethyl-2-phenylethyl acetate, 4-cyclohexyl-2-methyl-2-butanol, amyl salicylate, high cis methyl dihydrojasmonate, 3-methyl-5-phenyl-1-pentanol, verdyl proprionate, geranyl acetate, tetrahydro linalool, cis-7-P-menthanol, Propyl (S)-2-(1,1-dimethylpropoxy)propanoate, 2-methoxynaphthalene, 2,2,2-trichloro-1-phenylethyl acetate, 4/3-(4-hydroxy-4-methylpentyl)-3-cyclohexene-1-carbaldehyde, amylcinnamic aldehyde, 4-phenyl-2-butanone, isononyle acetate, 4-(1,1-diméthyléthyl)-1-cyclohexyl acetate, verdyl isobutyrate and/or mixture of methyl-ionones isomers;

Fruity ingredients: gamma undecalactone, 4-decanolide, ethyl 2-methyl-pentanoate, hexyl acetate, ethyl 2-methylbutanoate, gamma nonalactone, allyl heptanoate, 2-phenoxyethyl isobutyrate, ethyl 2-methyl-1,3-dioxolane-2-acetate and/or diethyl 1,4-cyclohexane dicarboxylate;

Green ingredients: 2,4-dimethyl-3-cyclohexene-1-carbaldehyde, 2-tert-butyl-1-cyclohexyl acetate, styrallyl acetate, allyl (2-methylbutoxy)acetate, 4-methyl-3-decen-5-ol, diphenyl ether, (Z)-3-hexen-1-ol and/or 1-(5, 5-dimethyl-1-cyclohexen-1-yl)-4-penten-1-one;

Musk ingredients: 1,4-dioxa-5,17-cycloheptadecanedione, pentadecenolide, 3-methyl-5-cyclopentadecen-1-one, 1,3,4,6,7,8-hexahydro-4,6,6,7,8,8-hexamethyl-cyclopenta-g-2-benzopyrane, (1S,1'R)-2-[1-(3',3'- dimethyl-1'-cyclohexyl)ethoxy]-2-methylpropyl propanoate, pentadecanolide and/or (1S,1'R)-[1-(3',3'-Dimethyl-1'-cyclohexyl)ethoxycarbonyl]methyl propanoate;

Woody ingredients: 1-(octahydro-2,3,8,8-tetramethyl-2-naphtalenyl)-1-ethanone, patchouli oil, terpenes fractions of patchouli oil, (1'R,E)-2-ethyl-4-(2',2',3'-trimethyl-3'-cyclopenten-1'-yl)-2-buten-1-ol, 2-ethyl-4-(2,2,3-trimethyl-3-cyclopenten-1-yl)-2-buten-1-ol, Methyl cedryl ketone, 5-(2,2,3-trimethyl-3-cyclopentenyl)-3-methylpentan-2-ol, 1-(2,3,8,8-tetramethyl-1,2,3,4,6,7,8,8a-octahydronaphthalen-2-yl)ethan-1-one and/or isobornyl acetate;

Other ingredients (e.g. amber, powdery spicy or watery): dodecahydro-3a,6,6,9a-tetramethyl-naphtho[2,1-b]furan and any of its stereoisomers, heliotropin, anisic aldehyde, eugenol, cinnamic aldehyde, clove oil, 3-(1,3-benzodioxol-5-yl)-2-methylpropanal and/or 3-(3-isopropyl-1-phenyl)butanal.

A perfumery base according to the invention may not be limited to the above mentioned perfuming co-ingredients, and many of these co-ingredients are in any case listed in reference texts such as the book by S. Arctander, Perfume and Flavor Chemicals, 1969, Montclair, N.J., USA, or its more recent versions, or in other works of a similar nature, as well as in the abundant patent literature in the field of perfumery. It is also understood that said co-ingredients may also be compounds known to release in a controlled manner various types of perfuming compounds.

By "perfumery adjuvant", it is meant here an ingredient capable of imparting additional added benefit such as a color, a particular light resistance, chemical stability, etc. A detailed description of the nature and type of adjuvant commonly used in perfuming composition cannot be exhaustive, but it has to be mentioned that said ingredients are well known to a person skilled in the art. One may cite as specific non-limiting examples the following: viscosity agents (e.g. surfactants, thickeners, gelling and/or rheology modifiers), stabilizing agents (e.g. preservatives, antioxidant, heat/light and or buffers or chelating agents, such as BHT), coloring agents (e.g. dyes and/or pigments), preservatives (e.g. antibacterial or antimicrobial or antifungal or anti irritant agents), abrasives, skin cooling agents, fixatives, insect repellants, ointments, vitamins and mixtures thereof.

It is understood that a person skilled in the art is perfectly able to design optimal formulations for the desired effect by admixing the above mentioned components of a perfuming composition, simply by applying the standard knowledge of the art as well as by trial and error methodologies.

An invention's composition consisting of at least one compound of formula (I) and at least one perfumery carrier consists of a particular embodiment of the invention as well as a perfuming composition comprising at least one compound of formula (I), at least one perfumery carrier, at least one perfumery base, and optionally at least one perfumery adjuvant.

According to a particular embodiment, the compositions mentioned above, comprise more than one compound of formula (I) and enable the perfumer to prepare accords or perfumes possessing the odor tonality of various compounds of the invention, creating thus a new building block for creation purposes.

For the sake of clarity, it is also understood that any mixture resulting directly from a chemical synthesis, e.g. a reaction medium without an adequate purification, in which the compound of the invention would be involved as a starting, intermediate or end-product could not be considered as a perfuming composition according to the invention as far as said mixture does not provide the inventive compound in a suitable form for perfumery. Thus, unpurified reaction mixtures are generally excluded from the present invention unless otherwise specified.

The invention's compound can also be advantageously used in all the fields of modern perfumery, i.e. fine or functional perfumery, to positively impart or modify the odor of a consumer product into which said compound of formula (I) is added. Consequently, another object of the present invention consists of a perfumed consumer product comprising, as a perfuming ingredient, at least one compound of formula (I), as defined above.

The invention's compound can be added as such or as part of an invention's perfuming composition.

For the sake of clarity, "perfumed consumer product" is meant to designate a consumer product which delivers at least a pleasant perfuming effect to the surface or space to which it is applied (e.g. skin, hair, textile, or home surface). In other words, a perfumed consumer product according to the invention is a perfumed consumer product which comprises a functional formulation, as well as optionally additional benefit agents, corresponding to the desired consumer product, and an olfactory effective amount of at least one invention's compound. For the sake of clarity, said perfumed consumer product is a non-edible product.

The nature and type of the constituents of the perfumed consumer product do not warrant a more detailed description here, which in any case would not be exhaustive, the skilled person being able to select them on the basis of his general knowledge and according to the nature and the desired effect of said product.

Non-limiting examples of suitable perfumed consumer product include a perfume, such as a fine perfume, a splash or eau de parfum, a cologne or a shave or after-shave lotion; a fabric care product, such as a liquid or solid detergent, a fabric softener, a liquid or solid scent booster, a fabric refresher, an ironing water, a paper, a bleach, a carpet cleaner, a curtain-care product; a body-care product, such as a hair care product (e.g. a shampoo, a coloring preparation or a hair spray, a color-care product, a hair shaping product, a dental care product), a disinfectant, an intimate care product; a cosmetic preparation (e.g. a skin cream or lotion, a vanishing cream or a deodorant or antiperspirant (e.g. a spray or roll on), a hair remover, a tanning or sun or after sun product, a nail product, a skin cleansing, a makeup); or a skin-care product (e.g. a soap, a shower or bath mousse, oil or gel, or a hygiene product or a foot/hand care products); an air care product, such as an air freshener or a "ready to use" powdered air freshener which can be used in the home space (rooms, refrigerators, cupboards, shoes or car) and/or in a public space (halls, hotels, malls, etc.); or a home care product, such as a mold remover, a furnisher care product, a wipe, a dish detergent or a hard-surface (e.g. a floor, bath, sanitary or a window-cleaning) detergent; a leather care product; a car care product, such as a polish, a wax or a plastic cleaner.

Some of the above-mentioned perfumed consumer products may represent an aggressive medium for the invention's compounds, so that it may be necessary to protect the latter from premature decomposition, for example by encapsulation or by chemically binding it to another chemical which is suitable to release the invention's ingredient upon a suitable external stimulus, such as an enzyme, light, heat or a change of pH.

The proportions in which the compounds according to the invention can be incorporated into the various aforementioned products or compositions vary within a wide range of values. These values are dependent on the nature of the article to be perfumed and on the desired organoleptic effect as well as on the nature of the co-ingredients in a given base when the compounds according to the invention are mixed with perfuming co-ingredients, solvents or additives commonly used in the art.

For example, in the case of perfuming compositions, typical concentrations are in the order of 0.001% to 10% by weight, or even more, of the compounds of the invention based on the weight of the composition into which they are incorporated. In the case of perfumed consumer product, typical concentrations are in the order of 0.01% to 5% by weight, or even more, of the invention's compounds relative to the total weight of the consumer product into which they are incorporated.

The invention's compounds can be prepared according to a method as described herein-below.

EXAMPLES

The invention will now be described in further detail by way of the following examples, wherein the abbreviations have the usual meaning in the art, the temperatures are indicated in degrees centigrade (° C.); NMR spectra were acquired using either a Bruker Advance II Ultrashield 400 plus operating at (400 MHz ($^1$H) and 100 MHz ($^{13}$C) or a Bruker Advance III 500 plus operating at (500 MHz ($^1$H) and 125 MHz ($^{13}$C) or a Bruker Advance III 600 cryoprobe operating at (600 MHz ($^1$H) and 150 MHz ($^{13}$C). Spectra were internally referenced and chemical shifts δ are indicated in ppm relative to TMS 0.0 ppm and coupling constants J are expressed in Hz.

Preparation of 3-(4-(2-hydroxy-2-methylpropyl)cyclohex-1-en-1-yl)propanal

Step 1: Ethyl 4-(4-methylpent-3-en-1-yl)cyclohex-3-ene-1-carboxylate

To a suspension of aluminum trichloride (3.33 g, 25 mmol, 0.1 equiv.) in toluene (58 mL) at 0° C. was added ethyl acrylate (27.1 mL, 250 mmol, 1 equiv.) dropwise, followed by myrcene (47.3 mL, 275 mmol, 1.1 equiv.). The solution was allowed to warm slowly to r.t. and stirred for 3 days at r.t. then quenched with a 5% HCl solution. The aqueous layer was removed, extracted with ether and the organic phase was washed with a saturated solution of sodium bicarbonate, dried over sodium sulfate, filtered, and the solvents evaporated under vacuum. The residue was used without further purification in the next step.

Step 2: (4-(4-methylpent-3-en-1-yl)cyclohex-3-en-1-yl)methanol

To a suspension of lithium aluminum hydride (9.47 g, 250 mmol, 1 equiv.) in THF (400 mL) at 0° C. was added a solution of ethyl 4-(4-methylpent-3-en-1-yl)cyclohex-3-ene-1-carboxylate (crude product from the previous step, 250 mmol, 1 equiv.) in THF (100 mL) dropwise while maintaining the temperature below 8° C. After stirring at 0° C. for 1 h, the reaction was quenched sequentially with 10 mL of water, 30 mL of a 5% NaOH solution and 10 mL of water. The suspension was filtered on a Celite pad using ether as an eluant and the solvents were evaporated under vacuum. The crude product was purified by bulb-to-bulb distillation (0.15-0.2 mbar, 130° C.) to afford the desired alcohol as an oil (45.5 g, 94% yield over two steps).

$^1$H NMR (CDCl$_3$, 600 MHz): 1.56 (s, 1H), 1.60 (s, 3H), 1.68 (s, 3H), 1.70-1.77 (m, 2H), 1.81-1.85 (m, 1H), 1.94-2.02 (m, 4H), 2.05-2.12 (m, 3H), 3.49-3.56 (m, 2H), 5.08-5.11 (m, 1H), 5.38-5.40 (m, 1H).

$^{13}$C NMR (CDCl$_3$, 150 MHz): 137.8 (s), 131.4 (s), 124.4 (d), 119.5 (d), 67.8 (t), 37.7 (t), 36.4 (d), 28.2 (t), 27.8 (t), 26.5 (t), 25.7 (q), 25.7 (t), 17.7 (q).

Step 3: (4-(4-methylpent-3-en-1-yl)cyclohex-3-en-1-yl)methyl methanesulfonate To a solution of (4-(4-methylpent-3-en-1-yl)cyclohex-3-en-1-yl)methanol (45.5 g, 234 mmol, 1 equiv.) and triethylamine (49.0 mL, 351 mmol, 1.5 equiv.) in dichloromethane (468 mL) at 0° C. was added methanesulfonyl chloride (21.9 mL, 281 mmol, 1.2 equiv.) dropwise. The reaction was stirred at r.t. for 5 minutes before being quenched with a saturated solution of ammonium chloride. It was extracted twice with ether, the combined organic extracts were washed twice with brine, dried over sodium sulfate, filtered and the solvents evaporated under vacuum. The residue was used without further purification in the next step.

Step 4: 4-(bromomethyl)-1-(4-methylpent-3-en-1-yl)cyclohex-1-ene

To a solution of (4-(4-methylpent-3-en-1-yl)cyclohex-3-en-1-yl)methyl methanesulfonate (crude product from the previous step, 234 mmol, 1 equiv.) in THF (586 mL) was added tetrabutylammonium bromide (91 g, 281 mmol, 1.2 equiv.) and the reaction was refluxed for 18 h. The solvent was evaporated, ether was added and the organic phase was washed twice with water and then brine, dried over sodium sulfate, filtered and the solvents evaporated under vacuum. The residue was purified by bulb-to-bulb distillation (0.15-0.2 mbar, 135° C.) to afford the desired bromide as an oil (57.7 g, 96% yield over two steps).

$^1$H NMR (CDCl$_3$, 600 MHz): 1.34-1.41 (m, 1H), 1.60 (s, 3H), 1.68 (s, 3H), 1.77-1.83 (s, 1H), 1.86-2.10 (m, 8H), 2.19-2.23 (m, 1H), 3.36 (d, J=6.5 Hz, 2H), 5.07-5.10 (m, 1H), 5.36 (m, 1H).

$^{13}$C NMR (CDCl$_3$, 150 MHz): 137.6 (s), 131.5 (s), 124.2 (d), 119.1 (d), 39.7 (t), 37.5 (t), 36.1 (d), 30.5 (t), 27.8 (t, 2C), 26.4 (t), 25.7 (q), 17.7 (q).

Step 5: 2-methyl-1-(4-(4-methylpent-3-en-1-yl)cyclohex-3-en-1-yl)propan-2-ol To a suspension of magnesium turnings (5.99 g, 246 mmol, 1.1 equiv.) and two drops of 1,2-dibromoethane (catalytic amount) in THF (5 mL) was added a few drops of 4-(bromomethyl)-4-methylpent-3-en-1-yl)cyclohex-1-ene and the mixture was refluxed. After the initiation was observed, a solution of remaining 4-(bromomethyl)-1-(4-methylpent-3-en-1-yl)cyclohex-1-ene (57.6 g, 224 mmol, 1 equiv.) in THF (220 mL) was added dropwise, while maintaining the reflux. Heating was continued for around 20 minutes after the addition was completed. The reaction was allowed to cool to r.t. (partial precipitation occurred) and acetone (24.7 mL, 336 mmol, 1.5 equiv.) was added dropwise while the temperature was maintained below 25° C. After stirring for 1 h, a saturated solution of ammonium chloride was added. The reaction was extracted three times with ether, the combined organic extracts were dried over sodium sulfate, filtered and the solvents evaporated under vacuum. The residue was purified by flash column chromatography on silica gel (Heptane/AcOEt 93:7) and bulb-to-bulb distillation (0.17-0.2 mbar, 125° C.) to afford the desired alcohol as an oil (16.6 g, 31% yield).

$^1$H NMR (CDCl$_3$, 600 MHz): 1.25 (s, 6H), 1.27-1.35 (m, 1H), 1.43 (A of ABX, J=14.2, 5.4 Hz, 1H), 1.48 (B of ABX, J=14.2, 5.4 Hz, 1H), 1.60 (s, 3H), 1.68 (s, 3H), 1.68-1.78 (m, 2H), 1.79-1.83 (m, 1H), 1.93-1.95 (m, 3H), 2.01-2.09 (m, 3H), 2.17-2.20 (m, 1H), 5.09-5.11 (m, 1H), 5.36 (m, 1H).

$^{13}$C NMR (CDCl$_3$, 150 MHz): 137.6 (s), 131.3 (s), 124.5 (d), 120.2 (d), 71.6 (s), 50.3 (t), 37.7 (t), 33.9 (t), 31.1 (t), 30.1 (q), 30.0 (d), 30.0 (q), 28.5 (t), 26.5 (t), 25.7 (q), 17.7 (q).

Step 6: 3-bromo-5-(4-(2-hydroxy-2-methylpropyl) cyclohex-1-en-1-yl)-2-methylpentan-2-ol To a solution of 2-methyl-1-(4-(4-methylpent-3-en-1-yl) cyclohex-3-en-1-yl)propan-2-ol (15.4 g, 65 mmol, 1 equiv.) in THF (354 mL) and water (215 mL) at 0° C. was added a solution of NBS (17.4 g, 98 mmol, 1.5 equiv.) in the same solvent mixture (569 mL) dropwise. The reaction was stirred at 0° C. for 1 h, extracted twice with AcOEt, the combined organic extracts were dried over sodium sulfate, filtered and the solvents were evaporated under vacuum. The residue was used without further purification in the next step.

Step 7: 1-(4-(2-(3,3-dimethyloxiran-2-yl)ethyl)cyclohex-3-en-1-yl)-2-methylpropan-2-ol To a solution of 3-bromo-5-(4-(2-hydroxy-2-methylpropyl)cyclohex-1-en-1-yl)-2-methylpentan-2-ol (crude product from the previous step, 65 mmol, 1 equiv.) in methanol (260 mL) was added potassium carbonate (8.99 g, 65 mmol, 1 equiv.) and the reaction was stirred at r.t. for 1 h. It was diluted with water and extracted twice with ether. The combined organic extracts were dried over sodium sulfate, filtered and the solvents evaporated under vacuum. The residue was purified by flash column chromatography on silica gel (Heptane/AcOEt 85:15 to 7:3) to afford an oil that was used directly in the next step.

Step 8: 3-(4-(2-hydroxy-2-methylpropyl)cyclohex-1-en-1-yl)propanal

To a solution of 1-(4-(2-(3,3-dimethyloxiran-2-yl)ethyl) cyclohex-3-en-1-yl)-2-methylpropan-2-ol (from the previous step, 65 mmol, 1 equiv.) in THF (300 mL) and water (150 mL) at 0° C. was added periodic acid (17.8 g, 78 mmol, 1.2 equiv.) portionwise. The reaction was allowed to warm slowly to r.t. and stirred for 30 min at r.t. Water was added and the mixture was extracted twice with ether. The combined organic extracts were washed with a 10% solution of sodium thiosulfate, washed with brine, dried over sodium sulfate, filtered and the solvents evaporated under vacuum. The residue was purified by flash column chromatography on silica gel (Heptane/AcOEt 8:2 to 7:3) and bulb-to-bulb distillation (0.17-0.2 mbar, 135° C.) to afford the desired aldehyde as an oil (6.00 g, 44% yield over three steps).

$^1$H NMR (CDCl$_3$, 600 MHz): 1.24 (s, 6H), 1.27-1.34 (m, 2H), 1.42 (A of ABX, J=14.2, 5.4 Hz, 1H), 1.48 (B of ABX, J=14.2, 5.4 Hz, 1H), 1.66-1.77 (m, 2H), 1.81-1.85 (m, 1H), 1.91-1.94 (m, 1H), 2.01-2.06 (m, 1H), 2.17-2.20 (m, 1H), 2.27-2.29 (m, 2H), 2.51-2.54 (m, 2H), 5.38 (m, 1H), 9.76 (t, J=1.8 Hz, 1H).

$^{13}$C NMR (CDCl$_3$, 150 MHz): 202.8 (d), 135.5 (s), 121.4 (d), 71.5 (s), 50.1 (t), 41.9 (t), 33.7 (t), 30.8 (t), 30.1 (q), 30.0 (q), 29.9 (d), 29.7 (t), 28.5 (t).

Example 2

Preparation of a Perfuming Composition

An olfactory evaluation of the 3-(4-(2-hydroxy-2-methylpropyl)cyclohex-1-en-1-yl)propanal obtained in Example 1 showed that it presents a floral, Lily of the valley and lilac odor.

In order to evaluate its contribution in a composition, a woman's perfume, was prepared by admixing the following ingredients:

| Ingredients | Part by weight |
|---|---|
| Benzyl acetate | 60 |
| Ethyl 3-oxobutanoate and (2Z)-ethyl 3-hydroxy-2-butenoate | 20 |
| Allyl (3-methylbutoxy)acetate and (+−)-allyl (2-Methylbutoxy)acetate | 20 |
| (−)-(3aR,5aS,9aS,9bR)-3a,6,6,9a-tetramethyldodecahydronaphto[2,1-b]furan | 20 |
| 10%* (+−)-ethyl 2-methylpentanoate | 20 |
| 7-methyl-2H-1,5-benzodioxepin-3(4H)-one | 20 |
| Cassis base | 120 |
| 3-methyl-2-[(2Z)-2-penten-1-yl]-2-cyclopenten-1-one | 40 |
| (+−)-3,7-dimethyl-6-octen-1-ol | 100 |
| Allyl (cyclohexyloxy)acetate | 10 |
| 10%* (2e)-1-(2,6,6-trimethyl-1,3-cyclohexadien-1-yl)-2-buten-1-one | 60 |
| (+−)-4-decanolide | 20 |
| 10%* (+−)-(e)-8-decen-5-olide and (+−)-(Z)-8-decen-5-olide | 20 |
| (+−)-2,6-dimethyl-7-octen-2-ol | 80 |
| Dipropylene glycol | 800 |
| 10%* 1-methoxy-4-(2-propen-1-yl)benzene | 40 |
| (Z)-3,7-dimethyl-1,6-nonadien-3-ol and (E)-3,7-dimethyl-1,6-nonadien-3-ol | 400 |
| (+−)-3-(3-isopropyl-1-phenyl)butanal | 20 |
| (+−)-4,6,6,7,8,8-hex amethyl-1,3,4,6,7,8-Hexahydrocyclopenta[g]isochromene | 1000 |
| (E)-3,7-dimethyl-2,6-octadien-1-ol | 300 |
| 10%* methyl 2-octynoate | 20 |
| Methyl 2-((1RS,2RS)-3-oxo-2-pentylcyclopentyl)acetate | 1000 |
| Methyl dihydrojasmonate with high amount of isomer cis | 1000 |
| (+−)-3-(1,3-benzodioxol-5-yl)-2-methylpropanal | 600 |
| (+−)-7-hydroxy-3,7-dimethyloctanal | 200 |
| 10%* indole | 40 |
| 10%* 2-methoxy-4-[(1e)-1-propen-1-yl]phenol | 20 |
| (+−)-2-methyl-3-[4-(2-methyl-2-propanyl)phenyl]propanal | 1000 |
| (+−)-3,7-dimethyl-1,6-octadien-3-ol | 200 |
| (+−)-2,6-dimethyl-5-heptenal | 20 |
| (+−)-(E)-3-methyl-4-(2,6,6-trimethyl-2-cyclohexen-1-yl)-3-buten-2-one | 400 |
| (+−)-3-methylcyclopentadecanone | 400 |
| 10%* (2RS,4SR)-4-methyl-2-(2-methyl-1-propen-1-yl)tetrahydro-2H-Pyran and (2RS,4RS)-4-methyl-2-(2-methyl-1-propen-1-yl)tetrahydro-2H-pyran | 10 |
| 2-phenylethanol | 100 |
| 10%* (Z)-3-hexen-1-ol | 80 |
| Orange oil | 10 |
| (3Z)-3-hexen-1-yl salicylate | 200 |
| (+−)-3-methyl-5-(2,2,3-trimethyl-3-cyclopenten-1-yl)-2-pentanol | 60 |
| (+−)-1-(3,5,5,6,8,8-hexamethyl-5,6,7,8-tetrahydro-2-naphthalenyl)ethanone | 600 |
| (+−)-(E)-4-methyl-3-decen-5-ol | 800 |
| (1RS,2RS)-2-(2-methyl-2-propanyl)cyclohexyl acetate and (1RS,2SR)-2-(2-methyl-2-propanyl)cyclohexyl acetate | 60 |
| 2,4-dimethyl-3-cyclohexene-1-carbaldehyde | 10 |
| | 10000 |

*in dipropyleneglycol

The addition of 800 parts by weight of 3-(4-(2-hydroxy-2-methylpropyl)cyclohex-1-en-1-yl)propanal obtained in Example 1 to replace 800 parts by weight of dipropylene glycol to the above-described composition imparted to the latter a floral-green, rose and ozonic connotation.

When instead of the invention's compound, the same amount of 3-(4-(1-hydroxy-2-methylpropan-2-yl)phenyl) propanal was used to replace 800 parts by weight of dipropylene glycol, the composition acquired a more floral-muguet, creamier and more powdery connotation.

When instead of the invention's compound, the same amount of 3-[4-(2-hydroxy-2-methylpropyl)phenyl]propanal was used to replace 800 parts by weight of dipropylene glycol, the composition acquired a rounder, more floral-muguet, fresher connotation with a moist effect resembling Lyral®.

When instead of the invention's compound, the same amount of Lyral® was used to replace 800 parts by weight of dipropylene glycol, the composition acquired a rounder, more floral-muguet, fresher connotation with a moist effect.

Lyral® and 3-[4-(2-hydroxy-2-methylpropyl)phenyl]propanal blend well with the ozone, watery and salicylate notes of the perfuming composition, 3-(4-(1-hydroxy-2-methylpropan-2-yl)phenyl)propanal blends particularly well with the salicylate and musky notes whereas the inventive compound 3-(4-(2-hydroxy-2-methylpropyl)cyclohex-1-en-1-yl)propanal blends particularly well with the green, rosy and watery notes.

Example 3

Preparation of a Perfuming Composition

A men's perfume was prepared by admixing the following ingredients:

| Ingredients | Part by weight |
| --- | --- |
| 1,1-dimethyl-2-phenylethyl acetate | 160 |
| (+−)-1,5-dimethyl-1-vinyl-4-hexenyl acetate | 160 |
| (+−)-1-phenylethyl acetate | 20 |
| 1%* hexyl acetate | 40 |
| (2E)-2-benzylideneoctanal | 160 |
| (−)-(3aR,5aS,9aS,9bR)-3a,6,6,9a-tetramethyldodecahydronaphtho[2,1-b]furan | 80 |
| 1%* methyl 2-aminobenzoate | 40 |
| 10%* (Z)-3,7-dimethyl-2,6-octadienal and (E)-3,7-dimethyl-2,6-octadienal | 40 |
| (+−)-3,7-dimethyl-6-octen-1-ol | 40 |
| 2-chromenone | 40 |
| Allyl (cyclohexyloxy)acetate | 20 |
| 10%* (+−)-(2E)-1-(2,6,6-trimethyl-2-cyclohexen-1-yl)-2-buten-1-one | 80 |
| (+−)-2,6-dimethyl-7-octen-2-ol | 400 |
| Dipropylene glycol | 800 |
| 3-(4-ethylphenyl)-2,2-dimethylpropanal and 3-(2-ethylphenyl)-2,2-dimethylpropanal | 40 |
| (+−)-4,6,6,7,8,8-hexamethyl-1,3,4,6,7,8-hexahydrocyclopenta[g]isochromene | 4600 |
| (E)-3,7-dimethyl-2,6-octadien-1-ol | 40 |
| Geranium rose oil | 40 |
| methyl 2-((1RS,2RS)-3-oxo-2-pentylcyclopentyl)acetate | 400 |
| (+−)-3-(1,3-benzodioxol-5-yl)-2-methylpropanal | 300 |
| 1-(octahydro-2,3,8,8-tetramethyl-2-naphtalenyl)-1-ethanone | 600 |
| Lavandin oil | 40 |
| (+−)-2-methyl-3-[4-(2-methyl-2-propanyl)phenyl]propanal | 800 |
| Methyl 2,4-dihydroxy-3,6-dimethylbenzoate | 80 |
| 10%* (2E,6Z)-2,6-nonadienal | 40 |
| 2-Methylbutyl salicylate and pentyl salicylate | 40 |
| (3Z)-3-hexen-1-yl salicylate | 40 |

-continued

| Ingredients | Part by weight |
| --- | --- |
| (+−)-3-methyl-5-(2,2,3-trimethyl-3-cyclopenten-1-yl)-2-pentanol | 400 |
| (+−)-1-(3,5,5,6,8,8-hexamethyl-5,6,7,8-tetrahydro-2-naphthalenyl)ethanone | 400 |
| 10%* (2E)-2-hexenal | 20 |
| 10%* 2,4-Dimethyl-3-cyclohexene-1-carbaldehyde | 40 |
| | 10000 |

*in dipropyleneglycol

The addition of 800 parts by weight of 3-(4-(2-hydroxy-2-methylpropyl)cyclohex-1-en-1-yl)propanal obtained in Example 1 to replace 800 parts by weight of dipropylene glycol to the above-described composition imparted to the latter a floral-green, rose and ozonic connotation.

When instead of the invention's compound, the same amount of 3-(4-(1-hydroxy-2-methylpropan-2-yl)phenyl) propanal was used to replace 800 parts by weight of dipropylene glycol, the composition acquired a more-floral-muguet, creamier and more powdery connotation.

When instead of the invention's compound, the same amount of 3-[4-(2-hydroxy-2-methylpropyl)phenyl]propanal was used to replace 800 parts by weight of dipropylene glycol, the composition acquired a rounder, more floral-muguet, fresher connotation with a moist effect resembling Lyral®.

When instead of the invention's compound, the same amount of Lyral® was used to replace 800 parts by weight of dipropylene glycol, the composition acquired a rounder, more floral-muguet, fresher connotation with a moist effect.

Lyral® and 3-[4-(2-hydroxy-2-methylpropyl)phenyl]propanal blend well with the ozone, watery, salicylate and oak moss notes of the perfuming composition, 3-(4-(1-hydroxy-2-methylpropan-2-yl)phenyl)propanal blends particularly well with the salicylate and musky notes whereas the inventive compound 3-(4-(2-hydroxy-2-methylpropyl)cyclohex-1-en-1-yl)propanal blends particularly well with the green, rosy and ozonic notes.

The invention claimed is:
1. A compound of formula

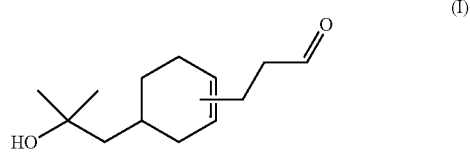

(I)

in the form of any one of its stereoisomers, regioisomers, or a mixture thereof,
wherein the compound has a floral-green, rose and ozonic organoleptic impression.
2. The compound according to claim 1, wherein the compound is

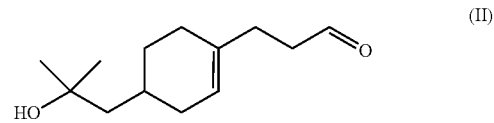

(II)

in the form of any one of its stereoisomers or a mixture thereof.

3. A method to confer, enhance, improve or modify the odor properties of a perfuming composition or of a perfumed article, which method comprises adding to said composition or article an effective amount of at least one compound of formula (I) as defined in claim 2.

4. A perfuming composition comprising:
   i) at least one compound of formula (I), as defined in claim 2;
   ii) at least one ingredient selected from the group consisting of a perfumery carrier and a perfumery base; and
   iii) optionally at least one perfumery adjuvant.

5. A perfumed consumer product comprising at least one compound of formula (I), as defined in claim 2.

6. A method to confer, enhance, improve or modify the odor properties of a perfuming composition or of a perfumed article, which method comprises adding to said composition or article an effective amount of at least one compound of formula (I) as defined in claim 1.

7. A perfuming composition comprising:
   i) at least one compound of formula (I), as defined in claim 1;
   ii) at least one ingredient selected from the group consisting of a perfumery carrier and a perfumery base; and
   iii) optionally at least one perfumery adjuvant.

8. A perfumed consumer product comprising a composition as defined in claim 7.

9. A perfumed consumer product comprising at least one compound of formula (I), as defined in claim 1.

10. The perfumed consumer product according to claim 9, wherein the product is a perfume, a fabric care product, a body-care product, a cosmetic preparation, a skin-care product, an air care product, or a home care product.

11. The perfumed consumer product according to claim 9, wherein the perfumery consumer product is a fine perfume, a splash or eau de parfum, a cologne, a shave or after-shave lotion, a liquid or solid detergent, a fabric softener, a fabric refresher, an ironing water, a paper, a bleach, a carpet cleaner, a curtain-care product, a shampoo, a coloring preparation, a color care product, a hair shaping product, a dental care product, a disinfectant, an intimate care product, a hair spray, a vanishing cream, a deodorant or antiperspirant, a hair remover, a tanning or sun product, a nail product, a skin cleansing, a makeup, a perfumed soap, shower or bath mousse, oil or gel, or a foot/hand care products, a hygiene product, an air freshener, a "ready to use" powdered air freshener, a mold remover, a furnisher care, a wipe, a dish detergent or hard-surface detergent, a leather care product, or a car care product.

* * * * *